United States Patent
D'Antonio

(10) Patent No.: US 9,117,356 B2
(45) Date of Patent: Aug. 25, 2015

(54) BABY MONITOR WITH BREAKAWAY CORD AND WIRELESS ALARM

(71) Applicant: Steven D'Antonio, Long Beach, NY (US)

(72) Inventor: Steven D'Antonio, Long Beach, NY (US)

(*) Notice: Subject to any disclaimer, the term of this patent is extended or adjusted under 35 U.S.C. 154(b) by 0 days.

(21) Appl. No.: 13/851,061

(22) Filed: Mar. 26, 2013

(65) Prior Publication Data

US 2013/0278419 A1 Oct. 24, 2013

Related U.S. Application Data

(60) Provisional application No. 61/685,874, filed on Mar. 26, 2012.

(51) Int. Cl.
*G08B 1/08* (2006.01)
*G08B 21/02* (2006.01)
*G08B 21/18* (2006.01)

(52) U.S. Cl.
CPC .......... *G08B 21/0202* (2013.01); *G08B 21/185* (2013.01); *G08B 21/0208* (2013.01); *G08B 21/0219* (2013.01)

(58) Field of Classification Search
CPC .......... G08B 21/0202; G08B 21/0208; G08B 21/0219; G08B 21/185; G08B 31/00
USPC ................. 340/539.15, 573.4, 568.2, 539.13, 340/825.14, 825.72, 825.08, 825.36
See application file for complete search history.

(56) References Cited

U.S. PATENT DOCUMENTS

| | | | |
|---|---|---|---|
| 5,745,037 A * | 4/1998 | Guthrie et al. | 340/573.4 |
| 2004/0111045 A1 * | 6/2004 | Sullivan et al. | 600/595 |
| 2006/0103522 A1 | 5/2006 | Spencer | |
| 2007/0085691 A1 * | 4/2007 | Singer et al. | 340/573.4 |
| 2007/0161262 A1 | 7/2007 | Lloyd | |
| 2010/0007486 A1 * | 1/2010 | Lu | 340/539.15 |
| 2010/0211080 A1 * | 8/2010 | Trivisani et al. | 606/120 |
| 2013/0307684 A1 * | 11/2013 | Pallotta | 340/539.11 |

* cited by examiner

*Primary Examiner* — Daniel Previl
(74) *Attorney, Agent, or Firm* — Ruth Eure

(57) ABSTRACT

The invention provides a baby monitor device featuring a specially designed power cord that easily separates from the monitor when handled or otherwise accessed. When the cord is separated from the monitor, an internal battery powered alarm immediately sounds and notifies a child's caregivers, allowing them to take immediate action to retrieve the cord and assist the child.

5 Claims, 2 Drawing Sheets

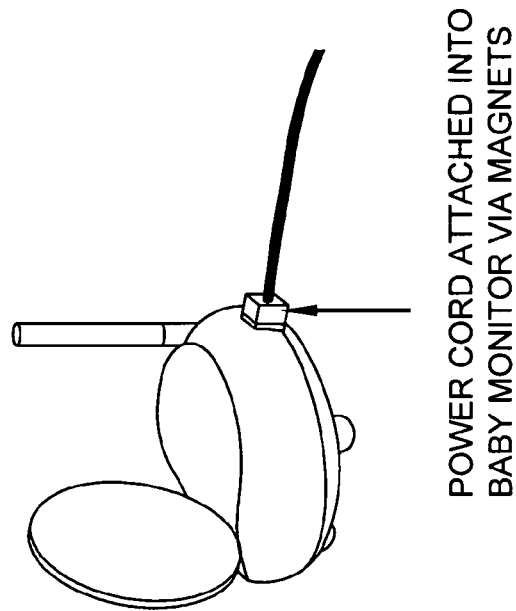
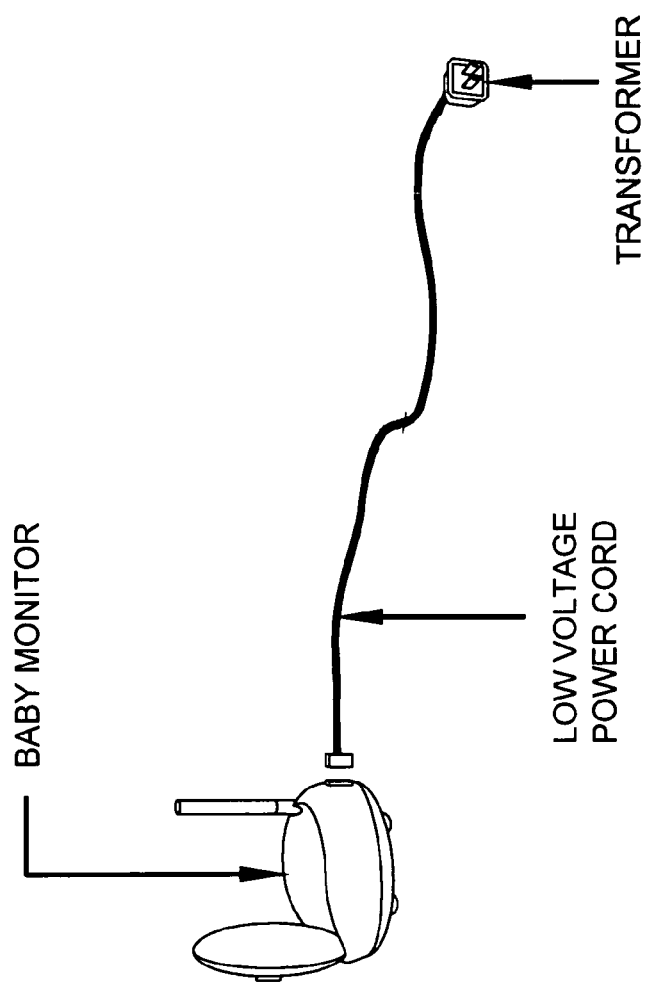

USB DEVICE (WIRELESS)
NOTIFICATION #2: MESSAGE
ON TV SCREEN

REMOTE HANDSET
NOTIFICATION #1: ALARM SOUNDS

BABY MONITOR WITH BREAKAWAY CORD AND WIRELESS ALARM

CLAIM OF PRIORITY

This patent application claims priority under 35 USC 119 (e) (1) from U.S. Provisional Patent Application Ser. No. 61/685,874 filed Mar. 26, 2012, of common inventorship herewith entitled, "Baby Monitor with Breakaway Power Cord and Wireless Alarm."

FIELD OF THE INVENTION

The present invention pertains to the field of infant accessories, and more specifically to the field of baby monitors.

BACKGROUND OF THE INVENTION

The prior art has put forth several designs for baby monitors. Among these are:

US Patent 2006/0103522 to Cathryn N. Spencer describes a baby monitor with multi sensory notification. The baby monitor comprises a first base and a second base each having a microphone for detecting sound and a radio component for broadcasting the detected sound as a unique radio signal unique to each base. The baby monitor also has a receiver which contains a speaker for broadcasting a reproduction of the detected sound, a first indicator light to indicate if the unique radio signal is a first unique radio signal, a second indicator light to indicate if the unique radio signal is a second unique radio signal, and a vibrating motor which issues a first vibratory alert when a first unique radio signal is received and a second vibratory alert when a second unique radio signal is received.

US Patent 2007/0161262 to James Taylor Lloyd describes a detachable magnetic electrical connector. A connector body attached to an appliance has a first body with four contact receptacles and a magnet which is adapted to attach and detach from a second body having four contact pins and a ferrous metal plate. The second body is attached to an electrical cord with a grounded plug. Two of the pins are the live electrical connections. The other two pins are ground connections that coexist, so the grounded connection for the appliance exists as long as one remains in contact. The two ground connections are spatially located relative to one another so that no matter which direction breakaway occurs, at least one will always be in connection until the live connection is broken first.

US Patent 2010/0007486 to Jan Jang Lu is a wireless infant state alarm system that includes a detecting device placed adjacent an infant. The detecting device includes an external signal receiver for receiving an external signal indicative of at least one of movement and sound of the infant. The detecting device further includes a signal transmitter receiving and converting the external signal into a wireless signal indicative of at least one of movement and sound of the infant and transmitting the wireless signal. An alarm device is placed adjacent a guardian of the infant and includes a signal receiver and a vibrator. The signal receiver receives the wireless signal from the signal transmitter, and the vibrator vibrates to alert the guardian of a state of the infant.

None of these prior art references describe the present invention.

SUMMARY OF THE INVENTION

It is an object of the present invention to provide a baby monitor with a breakaway power cord and a wireless alarm.

BRIEF DESCRIPTION OF THE DRAWINGS

FIG. 1 is a prototypical full side view showing a baby monitor, a low voltage power cord and a transformer.

FIG. 2 is a prototypical diagonal full view showing a baby monitor getting power by inductive charging and a power cord attached to the baby monitor with magnets.

DETAILED DESCRIPTION OF THE INVENTION

Figure 4:
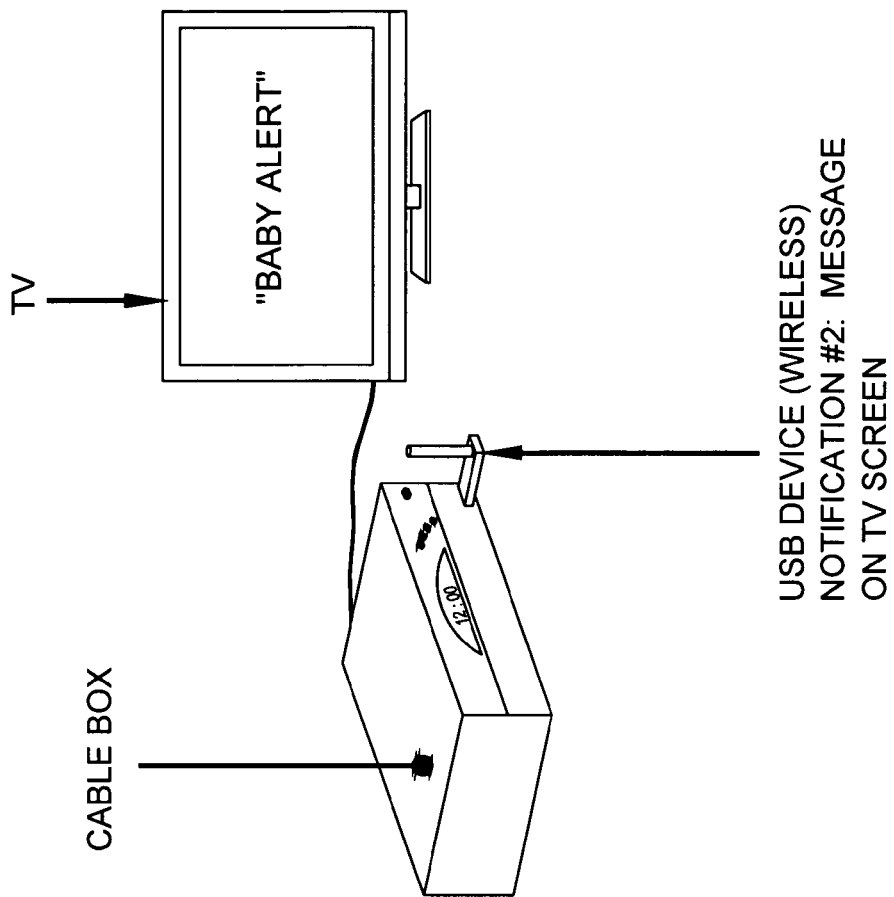
FIG. 4 is a diagonal front view of a cable box with wireless USB capability adjacent to a front view of a flat screen television that projects baby monitoring notification messages on its screen.
Figure 3:
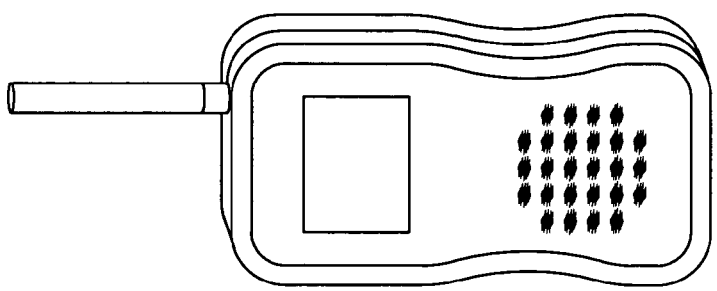
FIG. 3 is a prototypical front view of a remote handset that produces baby monitoring notifications by projecting alarm sounds through the handset's speaker.

The anticipated arrival of a new baby is an exciting and preparative time for soon to be parents. As a mother's belly swells, expectant parents attend birthing classes, read books and decorate nurseries to prepare for the arrival of a new child. Many thoughtful gifts and advice are received from friends and family members who throw baby showers honoring the blessed event. Nothing truly prepares parents for the hard work involved once a baby is actually born. Although birth and adoption are wonderful occasions, getting through the first few years of a child's development is extremely difficult. Fevers and tempers brought on by colic and teething render parents with concern, frustration and exhaustion due to sleepless nights rocking a restless infant. Snuggling a baby close to one's heart, comforting a crying infant and seeing a toddler take their first few steps make all pitfalls of parenting more than worthwhile. As parents adjust to schedules and needs of their newborns, sleepless nights and chaotic days give way to a more relaxed routine. Making sure their baby is healthy and happy is of utmost concern to most parents. Many parents utilize baby monitors when putting their child down for an afternoon nap or a night's sleep. A baby monitor is essentially a radio transmitter on a fixed frequency that puts out an FM signal as long as it is on. The monitor itself typically is placed in an infant's nursery next to the infant's crib, while the receiver is placed in a parent's bedroom, kitchen or other common area of the home. A child's movements and sounds transmit to the receiver, immediately alerting a parent when a child awakens or cries for attention.

Baby monitors are indeed practical accessories in households where infant children are present, but utilizing these monitoring systems present some safety hazards. The dangling cord of a baby monitor presents a serious strangulation hazard if the cord is in close enough proximity for the child to gain access. An inquisitive infant can reach for the cord from their crib and very easily wrap the cord about their body or neck while rolling over or moving about. Considering that monitor cords are permanently fixed to the monitor or held in place with secure interlocking female and male fittings, the cord becomes tighter as an infant struggles to pull free. The cord becomes tangled about the child's body or neck, leading to serious injury and possibly death. Infant strangulation deaths due to fixed cords on baby monitors initiated massive manufacturer recalls of baby monitors in the years of two thousand ten and two thousand eleven.

The present invention, hereinafter referred to as the Baby Monitor with Breakaway Power Cord and Wireless Alarm, is a baby Monitor featuring a specially designed power cord that easily separates from the monitor when handled or otherwise accessed. When the cord is separated from the monitor, an internal battery powered alarm immediately sounds and notifies a child's caregivers, allowing them to take immediate action to retrieve the cord and assist the child. Similar in operational function to traditional baby monitors, the Baby Monitor with Breakaway Power Cord and Wireless Alarm is a two piece unit comprised of a monitor transmitter and corresponding handheld receiver. The transmitter and receiver are manufactured of a heavy duty plastic material for housing electronic components and circuitry. The actual monitor is generally oval in shape and measures approximately four inches in diameter by approximately two to three inches in total height. Similar in general size and appearance to a wireless telephone handset or walkie talkie, the receiver stands upright on any flat surface area. The monitor transmitter and receiver handset both contain adjustable antennas that ensure a sizable working range for the device. The Baby Monitor with Breakaway Power Cord and Wireless Alarm projects a range of approximately one hundred fifty feet. A speaker is incorporated into the receiver handset for transmitting sounds that are sent by the monitor over a one way radio frequency. Operational controls including an on and off switch and volume control are located in an easily accessed position on the monitor transmitter and receiver respectively. The monitor is powered by a standard one hundred ten volts and sixty hertz electrical power with a detachable power cord designed for use with any two prong electrical outlet. A replaceable battery provides a backup power source for the monitor and also controls the present invention's alarm function. The most notable aspect of the Baby Monitor with Breakaway Power Cord and Wireless Alarm's design is shown in the functionality of its power cord and audible alarm. As opposed to a fixed physical connection to the baby monitor or tightly secured in place with interlocking male and female connector fittings, the Baby Monitor with Breakaway Power Cord and Wireless Alarm's power cord is attached to the monitor with a simple magnetic fastener and provides power to the monitor and internal battery with inductive charging. A fitting located on a proximal end of the power cord comprises a positive magnet, while a corresponding fitting located on the monitor's back side comprises a negative magnet. These two magnets naturally attract to one another and secure the cord in place. Although providing a secure connection between a power source and a monitor, these magnetic fasteners are easily disconnected by a light or gentle handling of the cord with very little force exerted. If an infant attempts to grab the cord and pull it into a crib or playpen, the cord immediately breaks from the monitor. When the cord is separated from the monitor in such a manner, an internal alarm is activated immediately and powered by means of an internal battery. Activating this alarm sends a signal to a companion receiver handset and initiates a loud and piercing alert sound that is emitted through the receiver's speakers. A parent is alerted instantly that the power cord is detached from the monitor and needs their immediate attention. This alarm continues until the power cord is affixed again to the monitor with the magnetic fasteners. A power switch for manually disarming the alarm is included in the receiver handset. The Baby Monitor with Breakaway Power Cord and Wireless Alarm contains a second wireless receiver that is connectable to a standard cable, satellite or digital box with a USB connection cable. This receiver is configured to send a visual notification across the user's television screen that the alarm has been activated with a message reading BABY ALERT. If the parent is enjoying a television program or video when the alarm sounds, they are visually notified to the situation and can assist a child instantly.

Application and use of the Baby Monitor with Breakaway Power Cord and Wireless Alarm is very simple and straight forward. Following package instructions, a user prepares the Baby Monitor with Breakaway Power Cord and Wireless Alarm for use. Installing appropriate batteries in both the monitor transmitter and the receiver handset, the user then places the monitor in an infant's bedroom, setting the monitor on a flat surface and plugging the power cord into a wall outlet using the cord's two pronged adapter plug. The user secures an opposite end of the cord to the monitor using the corresponding magnetic fasteners. The user places a companion receiver unit in a common area of the home, making sure to position the device within close proximity of their physical location. Upon putting an infant down for an afternoon nap or a nighttime rest, the parent or caregiver activates the Baby Monitor with Breakaway Power Cord and Wireless Alarm. As a caregiver monitors an infant's activity with the Baby Monitor with Breakaway Power Cord and Wireless Alarm, that caregiver hears noises emitted from the infant such as crying and coughing. In the event a child accesses the unit's power cord, the magnetic bond which secures the cord to the monitor breaks away and the cord immediately pulls free from the monitor, in turn activating the unit's internal alarm. Wirelessly sending a signal to the receiver unit, an alarm then sounds in a piercing audible alert that instantly informs the parent the child accessed the monitor's cord and needs immediate attention. If a caregiver is watching television when this incident occurs, a message is sent to the attached cable or satellite receiver, emitting a continuous alert message across the television screen. The parent then takes immediate action to tend to the child, effectively thwarting any injury or physical harm caused by a loose power cord.

The Baby Monitor with Breakaway Power Cord and Wireless Alarm is a practical and improved invention that provides consumers with a significantly safer alternative to traditional baby monitors. A cleverly designed baby monitor featuring a breakaway power cord that instantly disconnects from the monitor when a child accesses the cord, the Baby Monitor with Breakaway Power Cord and Wireless Alarm significantly reduces the threat of strangulation associated with standard fixed or fastened power cords. A fully functioning baby monitor, the Baby Monitor with Breakaway Power Cord and Wireless Alarm enables parents of newborn and infant children to constantly monitor their baby as the child sleeps or is left alone in their crib. Transmitting even the slightest sounds made by the infant, the Baby Monitor with Breakaway Power Cord and Wireless Alarm enables parents to easily monitor their child's activity without ever entering the child's bedroom. Parents and caregivers easily observe children without disturbing a child's slumber. Lightweight and portable, the Baby Monitor with Breakaway Power Cord and Wireless Alarm is installed easily and activated in a manner of minutes. Manufactured of quality materials, the present invention will withstand years of repeated use.

Although this invention has been described with respect to specific embodiments, it is not intended to be limited thereto and various modifications which will become apparent to the person of ordinary skill in the art are intended to fall within the spirit and scope of the invention as described herein taken in conjunction with the accompanying drawings and the appended claims.

The invention claimed is:

1. A baby monitor device with a breakaway power cord and a wireless alarm, comprising: a baby monitor having a power cord that easily separates from the baby monitor when handled or otherwise accessed sounding an internal battery powered alarm and notifying a child's caregivers, allowing the child's caregivers to take immediate action to retrieve the power cord and assist the child wherein the baby monitor device comprises a two piece unit comprised of a baby monitor transmitter and corresponding handheld receiver, and wherein the power cord is attached to the monitor with a magnetic fastener and provides power to the monitor and internal battery with inductive charging, further comprising a fitting located on a proximal end of the power cord comprising a positive magnet, while a corresponding fitting located on the monitor's back side comprises a negative magnet.

2. The baby monitor device of claim 1 further comprising an internal alarm activated immediately when the power cord is separated from the baby monitor, and powered by means of an internal battery, wherein the alarm sends a signal to the baby monitor receiver handset and initiates a loud and piercing alert sound that is emitted through baby monitor receiver's speakers.

3. The baby monitor device of claim 2, wherein the alarm continues until the power cord is affixed to the baby monitor with the magnetic fasteners.

4. The baby monitor device of claim 2, further comprising a power switch for manually disarming the alarm included in the receiver handset.

5. The baby monitor device of claim 2, further comprising a second wireless receiver that is connectable to a standard cable, satellite or digital box with a USB connection cable, wherein the second wireless receiver is configured to send a visual notification across the user's television screen that the alarm has been activated with a message reading BABY ALERT.

\* \* \* \* \*